United States Patent
Hasemann

(10) Patent No.: US 6,406,525 B1
(45) Date of Patent: Jun. 18, 2002

(54) ORGANIC COMPOUNDS

(75) Inventor: Ludwig Hasemann, Müllheim-Niederweiler (DE)

(73) Assignee: Clariant Finance (BVI) Limited, Tortola (VG)

( * ) Notice: Subject to any disclaimer, the term of this patent is extended or adjusted under 35 U.S.C. 154(b) by 0 days.

(21) Appl. No.: 09/969,312

(22) Filed: Oct. 2, 2001

Related U.S. Application Data

(63) Continuation of application No. 09/293,701, filed on Apr. 16, 1999, now abandoned.

(30) Foreign Application Priority Data

Apr. 18, 1998 (GB) ................................................ 9808167
Apr. 27, 1998 (GB) ................................................ 9808778

(51) Int. Cl.[7] ........................ C09D 11/02; C09D 498/22; C09B 67/22
(52) U.S. Cl. ........................ 106/31.47; 106/498; 8/549; 8/638; 544/75; 544/76
(58) Field of Search ............................. 106/31.47, 498; 8/549, 638; 544/75, 76

(56) References Cited

U.S. PATENT DOCUMENTS

| | | | |
|---|---|---|---|
| 3,883,523 A | 5/1975 | Parton | 544/76 |
| 5,068,327 A | 11/1991 | Miyamoto et al. | 544/76 |
| 5,122,605 A | 6/1992 | Pedrazzi | 544/76 |
| 5,213,582 A | 5/1993 | Wild et al. | 8/506 |
| 5,223,000 A | 6/1993 | Lauk | 8/638 |
| 5,268,475 A | 12/1993 | Lauk | 544/75 |
| 5,410,041 A | 4/1995 | Müller | 544/76 |
| 5,439,486 A | 8/1995 | Lauk | 8/532 |
| 5,451,665 A | 9/1995 | Tzikas | 544/76 |
| 5,585,489 A | 12/1996 | Russ et al. | 544/76 |
| 5,653,773 A | 8/1997 | Reddig et al. | 8/532 |
| 5,880,282 A | 3/1999 | Harm et al. | 544/76 |
| 5,969,258 A | 10/1999 | Schumacher et al. | 544/76 |
| 5,972,084 A | 10/1999 | Lacroix et al. | 106/31.47 |

FOREIGN PATENT DOCUMENTS

| | | |
|---|---|---|
| EP | 0 373 534 | 6/1990 |
| EP | 0 485 329 | 5/1992 |
| EP | 0 773 264 | 5/1997 |
| FR | 1 572 030 | 6/1969 |
| WO | 93/18224 | 9/1993 |

OTHER PUBLICATIONS

PCT International Search Report for Application No. 99/00659, mail date Jul. 9, 1999.
Chemical Abstract 73:89398p for FR 1572030, Jun. 20, 1969.

Primary Examiner—Helene Klemanski
(74) Attorney, Agent, or Firm—Andrew F. Sayko, Jr.

(57) ABSTRACT

New dioxazine compounds and mixtures thereof containing sulphonic acid groups according to formula (I)

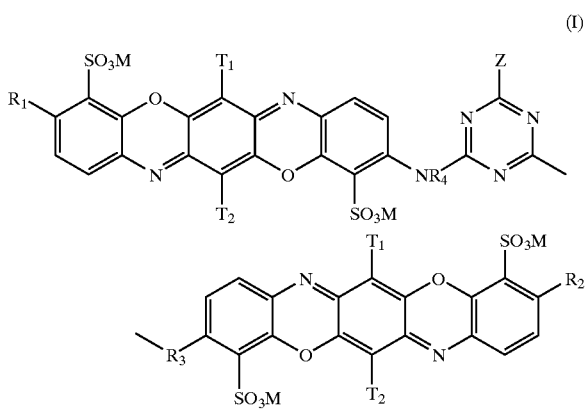

in which the substituents have the meanings given in claim 1, processes for their production and the use of such compounds for dyeing or printing organic substrates or as a component of printing inks.

5 Claims, No Drawings

ORGANIC COMPOUNDS

This application is a continuation application of copending application Ser. No. 09/293,701 filed on Apr. 16, 1999 now abandoned.

The invention relates to dioxazine compounds containing sulphonic acid groups and salts thereof and mixtures of these compounds which may be in internal or external salt form. They are suitable for use as dyestuffs.

According to the invention there are provided compounds of formula (I)

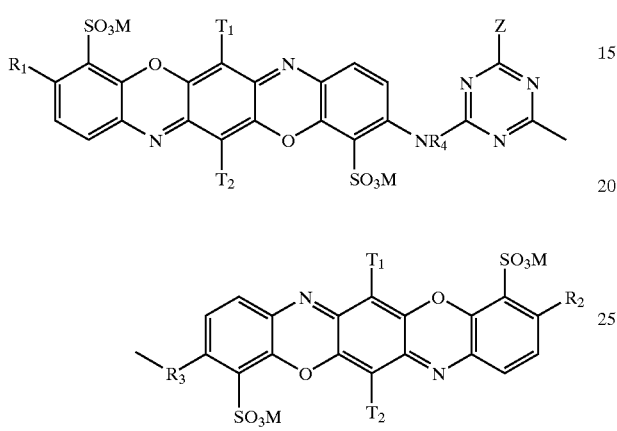

(I)

wherein
R$_1$ signifies —NH$_2$ or

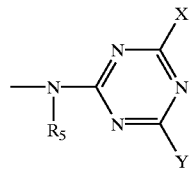

wherein
R$_5$ signifies hydrogen or C$_{1-4}$-alkyl,
X and Y independently signify halogen or hydroxy or C$_{1-3}$-alkoxy or phenoxy or the radical of a cyclic, an aliphatic, an araliphatic or an aromatic amine linked over the amine-nitrogen and optionally substituted by hydroxy, carboxy, alkoxy, alkyl and/or sulphonic acid groups or the rest of a heterocyclic amine linked over the amine-nitrogen,
Z signifies halogen or the radical of a cyclic, an aliphatic or an araliphatic amine linked over the amine-nitrogen and optionally substituted by hydroxy, carboxy, alkoxy and/or sulphonic acid groups or the rest of a heterocyclic amine linked over the amine-nitrogen,
R$_2$ signifies —NH$_2$ or

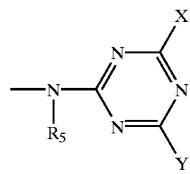

with the same definitions for R$_5$, X and Y as above or R$_2$ is the moiety (b)

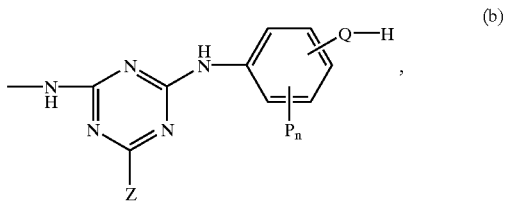

(b)

wherein
P signifies —SO$_3$H, —COOH or —OH,
Q signifies a —NH— radical or a group selected from

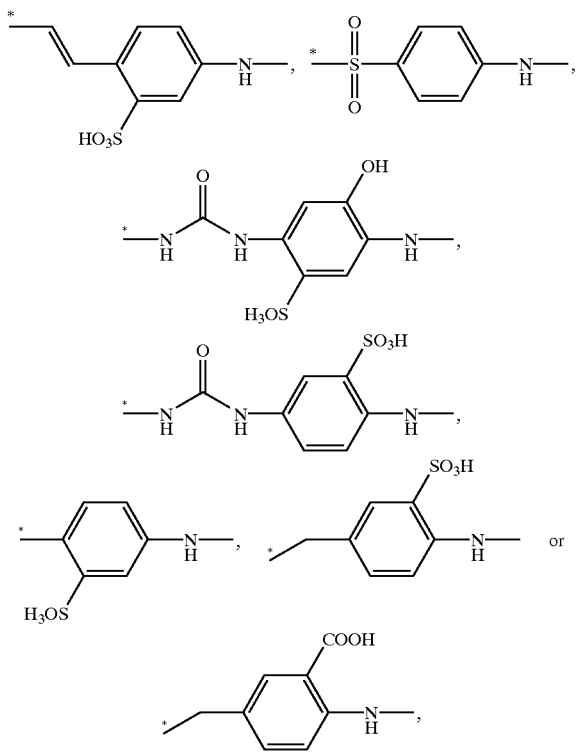

wherein the asterisk marks the bond attached to the phenyl ring,
Z signifies the same as above,
n has the value 0, 1, 2,
R$_3$ signifies —NR$_6$
in which R$_6$ signifies hydrogen or a C$_{1-4}$-alkyl radical or
R$_3$ is the rest (a)

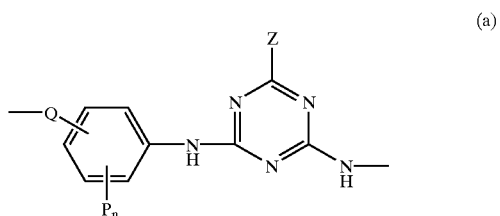

(a)

wherein all substituents have the same meanings as defined above, $R_4$ signifies hydrogen or $C_{1-4}$-alkyl, $T_1$ and $T_2$ independently from each other signify hydrogen, halogen, $C_{1-6}$-alkyl or $C_{1-4}$-alkoxy, M signifies hydrogen or a cation;

salts thereof and mixtures of such compounds and/or salts.

Preferred compounds of formula (I), wherein all substituents have same meanings as defined above, have the provisos that (i) when $R_1$ and $R_2$ is —$NH_2$ then $R_3$ is

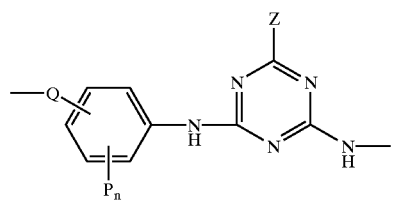
(a)

wherein P, Q, Z and n have the same meanings as defined above, (ii) when $R_1$ is —$NH_2$ and $R_2$ is

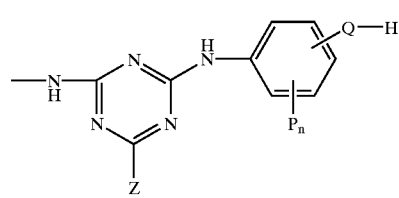
(b)

wherein P, Q, Z and n have the same meaning as defined above, then $R_3$ is —NH—;

salts thereof and mixtures of such compounds and/or salts.

In further preferred compounds of formula (I) both $R_1$ and $R_2$ signify

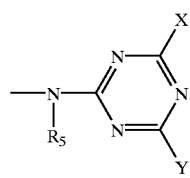

wherein $R_5$ signifies hydrogen or $C_{1-4}$-alkyl, and $R_3$ signifies —$NR_6$ in which $R_6$ signifies hydrogen or a $C_{1-4}$-alkyl radical and all the other substituents have the definition as defined above, salts thereof and mixtures of such compounds and/or salts.

In further preferred compounds the radicals X, Y and Z contain no chromophoric group.

In other preferred, compounds any amine H—X, H—Y or H—Z has a molecular weight in the range of 50 to 500, preferably 50 to 400. Where such an amine contains ring systems, it preferably contains 1 to 4 rings and most preferably has only 1 or 2 rings. Such amine preferably contains at least one hydrophilic group which independently can be anionic, cationic or non-ionogenic. Examples of anionic hydrophilic groups are carboxy or sulphonic acid groups. Examples of cationic hydrophilic groups are mono-($C_{1-4}$-alkyl)- or di($C_{1-4}$-alkyl)amino groups comprising a protonatable nitrogen atom or a quaternary ammonium group, wherein each $C_{1-4}$-alkyl group can be substituted by halogen, hydroxy, $C_{1-4}$-alkoxy, phenyl or phenoxy. Any phenyl or naphthyl ring present in the amine may be unsubstituted or substituted by one, two or three groups selected from halogen, hydroxy, $C_{1-4}$-alkyl, $C_{1-4}$-alkoxy, phenoxy, carboxy or sulphonic acid. Any heterocyclic ring present in the amine is a 5- or 6-membered ring containing one or two hetero atoms selected from N, O or S, which heterocyclicring is unsubstituted or substituted by one or two $C_{1-4}$-alkyl groups.

Preferred H—Z are ammonia and aliphatic amines, preferably substituted with a hydroxy, carboxy, alkoxy or sulphonic acid group, e.g. ethanolamine, diethanolamine, isopropanolamine, diisopropanolamine, 2-aminohydroxypropane, glycine, N-methyl-ethanolamine, 3-methoxy-propylamine, 1-aminoethyl-2-sulfonic acid and most preferably, 1-methylamino-ethyl-2-sulfonic acid; heterocyclic amines, e.g. morpholine, piperazine or hydroxyethylpiperazine; or N,N-diethylaminopropylamine and 1,2-diaminopropane.

Most preferred H—Z is 1-methylamino-ethyl-2-sulfonic acid.

In a further preferred compound or mixture M is hydrogen or a colorless cation or M is a cationic portion in a substituent X, Y or Z containing a cationic charge, to form an inner salt.

In a further aspect of the present invention there are provided mixtures containing a) a compound of formula (Ia) C

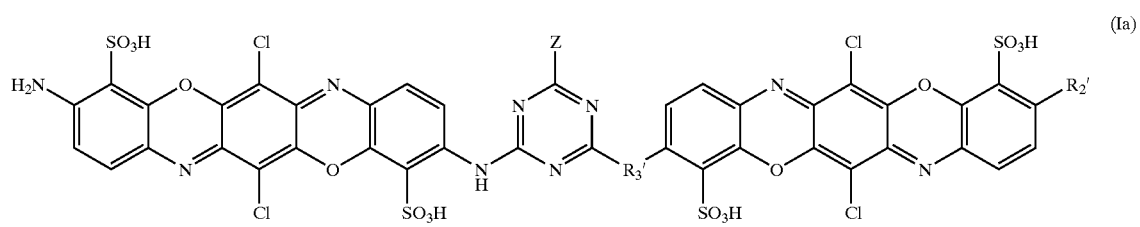
(Ia)

wherein $R_3'$ is a divalent radical of formula (a), $R_2'$ is —$NH_2$ and Z has the same meaning as defined above;

b) a compound of the above formula (Ia) wherein $R_3'$ is —NH—, $R_2'$ is a radical of formula (b) and Z has the same meaning as defined above;

c) a compound of formula (II)

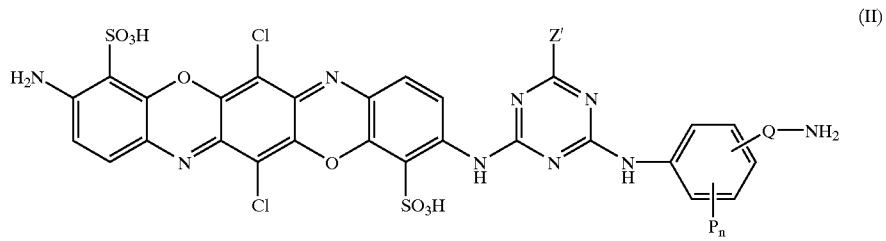

(II)

wherein Q, P and n have the same meaning as defined above and Z' has the same definition as Z, additionally Z' can be an aromatic amine, preferably for the component c) Z' is a radical of formula (c)

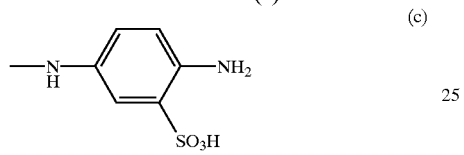

(c)

d) a compound of formula (II), wherein Z has the same meanings as defined above, except halogen, preferably for the component d) Z' is a radical of formula (d)

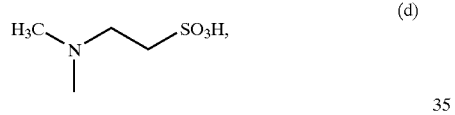

(d)

e) a compound of formula (III)

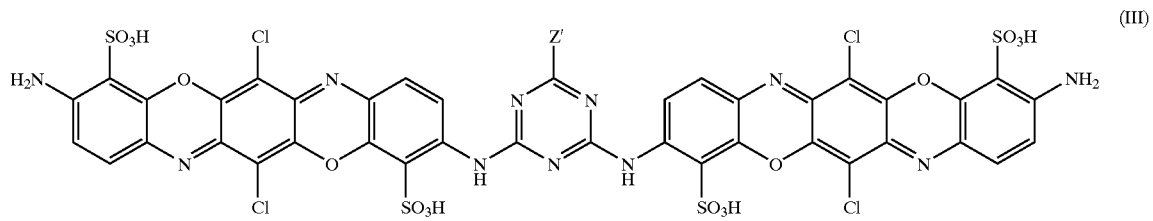

(III)

wherein Z' has the definition as defined above, or salts of such compounds.

The present invention further provides a process for the preparation of a compound of formula (Ib)

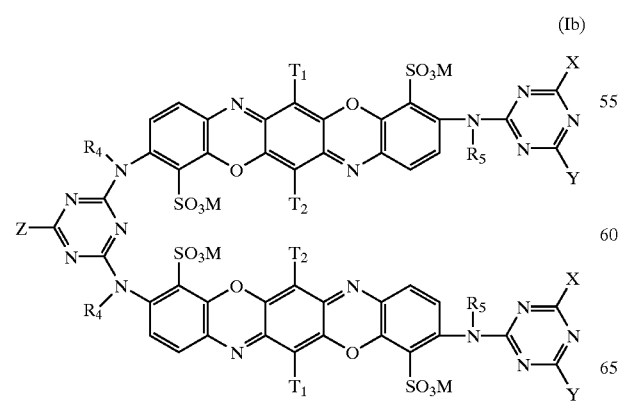

(Ib)

according to formula (I) with the same definitions of the substituents as defined above,
wherein one mole of a compound of formula (IV)

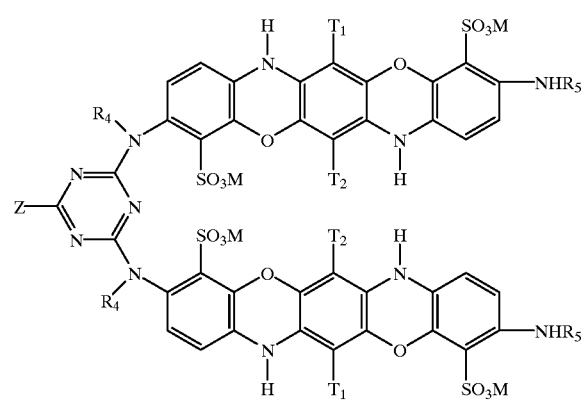

(IV)

or a mixture of compounds of formula (IV) with the same definitions of the substituents as in formula (Ib) is reacted with two moles of at least one compound of formula (V)

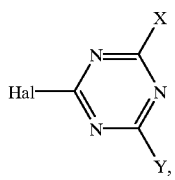

(V)

wherein Hal signifies halogen, preferably chlorine, and X and Y independently have the same meanings as defined above, under dehydrohalogenating conditions, and, if in formula (Ib) anyone of X and Y has a significance other than halogen while in formula (V) the corresponding X or Y signifies halogen, and/or if in formula (Ib) Z has a significance other than halogen, the obtained condensation product of formula (VI)

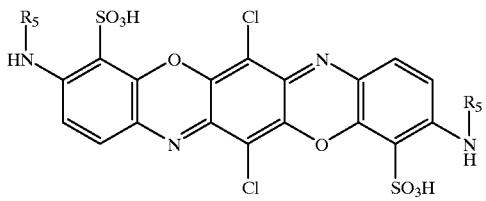

(VII)

which can be identical or different, depending on the meanings of $R_5$.

Before the reaction with a compound of the formula (V), the intermediately obtained dyestuff is brought into the leuco form of formula (IV) by reduction. This reduction process can be performed catalytically with hydrogen (and the usual catalysts palladium, platinum or nickel) or with other metals like iron, tin or zinc in the presence of acids. Alternatively, the reduction can be performed with sodium dithionite in water at pH values from 6 to 9, preferably 6.5 to 7.5, and

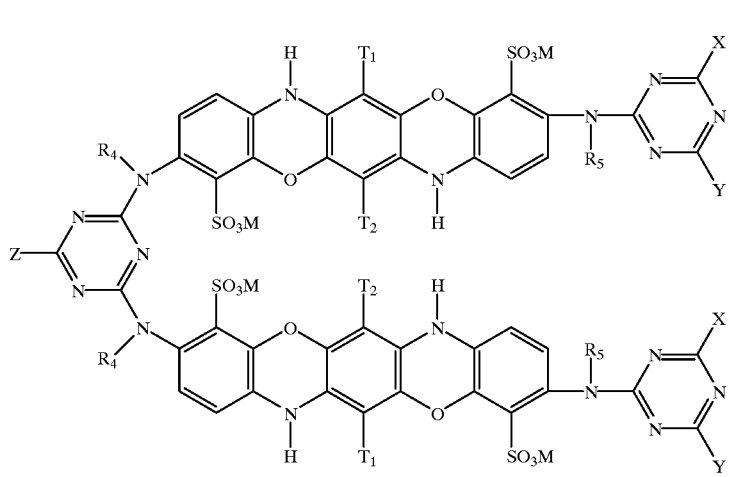

(VI)

with the same definitions of the substituents as in formula (Ib) is reacted, with at least one corresponding amine of formula H—X H—Y and/or H—Z, which have the same definitions as above and/or an alkali metal $C_{1-3}$-alcoholate or phenolate, as required. The oxidation of the leuco form to the dioxazine form takes place after the condensation step(s) or simultaneously with the exchange of halogen for amine.

The compounds of formula (Ib) thus obtained may be isolated in accordance with known methods.

The compounds of formula (Ib) containing free basic groups may be converted wholly or in part into water-soluble salts by reacting with any inorganic or organic acids. The compounds of formula (Ib) containing carboxy or sulphonic acid groups may also be converted into water-soluble salts by reacting with any basic compound.

The starting compounds, the amines of formula (IV) in the leuco form may be prepared by step-wise replacement of the chlorine atoms of cyanuric chloride whereby in a first and second step cyanuric chloride is reacted with a dioxazine compound of formula (VII)

temperatures from 15 to 45° C., preferably 20 to 30° C. The reducing agent is suitably used in double or triple molar amounts of the dyestuff to be reduced and all reduction and condensation reactions are performed in inert atmosphere, e.g. under nitrogen.

The compounds of formula (V) may also be prepared by step-wise replacement of the chlorine atoms of cyanuric chloride whereby in a first and/or second step, cyanuric chloride is reacted with an amine of formula HX and/or an amine of formula HY.

In the case where identical amino groups have to be introduced, this first and second steps may be combined into one step. Suitably, the single step is carried out at temperatures from 0–30° C. and preferably at pH 4–6.

Where different amino groups have to be introduced, suitably, the amine showing the higher selectivity with respect to the condensation reaction is introduced in the first step at a temperature of preferably 0–20° C. more preferably 0–5° C. Both condensation steps may be carried out using the conventional reaction medium where the upper limit of pH is 7. The second step is preferably carried out at 10–40° C., more preferably 12–30° C.

The starting compounds of formulae (VI), HX and HY are either known or may be prepared in accordance with known methods from available starting materials.

The present invention further provides a process for the preparation of compounds of the formula (Ia),

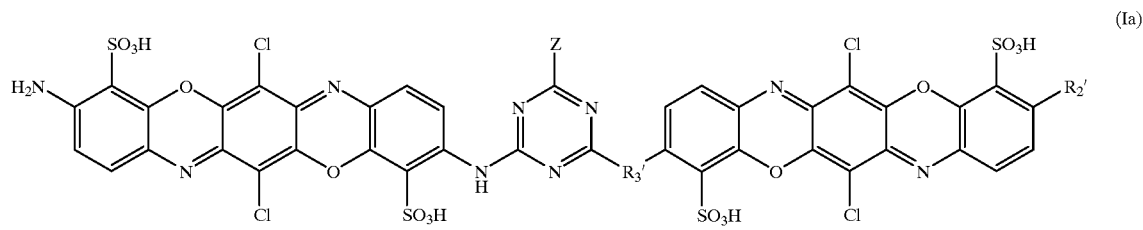

according to formula I wherein either
R$_3$' is a divalent radical of formula (a)

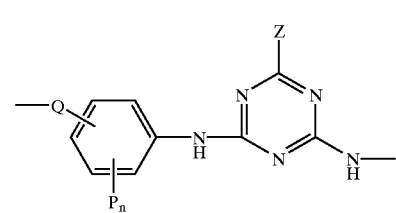

wherein P, Q, Z and n have the same meanings as defined above and R$_2$' is —NH$_2$; or
R$_3$' is —NH— and
R$_2$' is a radical of formula (b)

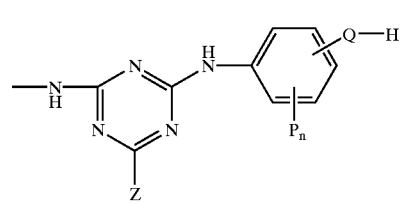

wherein P, Q, Z and n have the same meanings as defined above,
salts thereof and of mixtures of such compounds and/or salts, which comprises reacting a compound of formula (VIII)

wherein either R$_3$" is a divalent radical of formula (a')

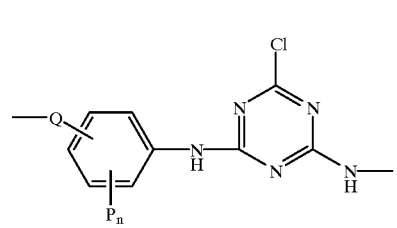

wherein P, Q and n have the same meanings as defined above
and R$_2$" is —NH$_2$; or R$_3$" is —NH— and R$_2$" is a radical of formula (b')

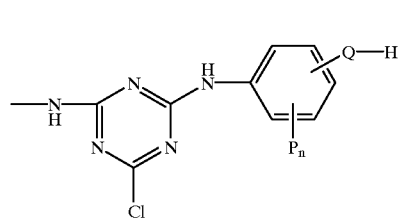

wherein P, Q and n have the same meanings as defined above or a mixture of such compounds with an amine H—Z or H—Z' and, if desired, converting compounds of formula (I) thus obtained into salts or salts thus obtained into compounds of formula (I) or into other salts.

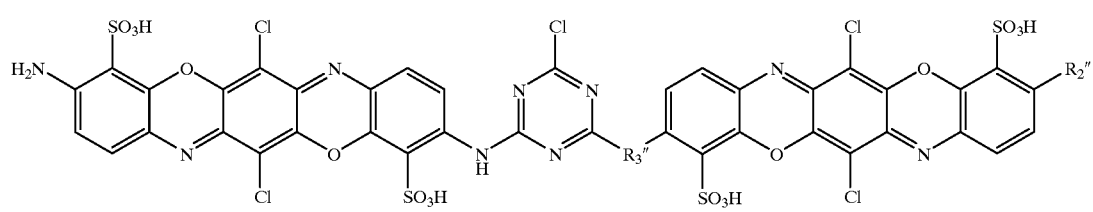

The compounds of the above formula (VIII) can be prepared by reacting a compound of formula (IX)

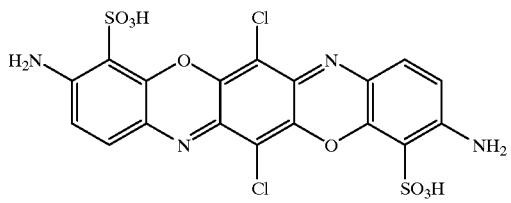

with about one equivalent of 2,4,6-trichlorotriazine, reacting the product of formula (X)

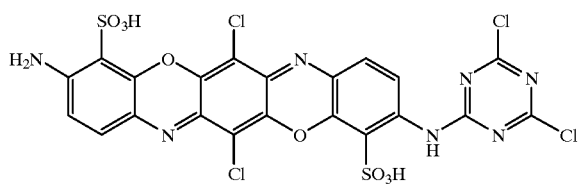

thus obtained with 1,4-diaminobenzene-2-sulfonic acid and reacting the product (XI)

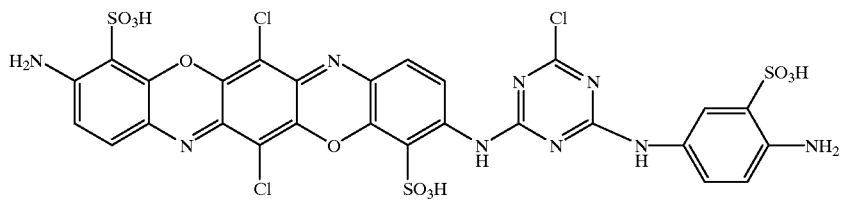

thus obtained with another portion of the compound of the above formula (X).

The compound of the above formula (X) can react (rather than with the 1,4-diaminobenzene-2-sulfonic acid) with any unreacted compound of the above formula (IX) and thus give a compound corresponding to the above formula (III) but in which Z' is chloro which, in the ultimate treatment with an amine H—Z', gives a compound of the above formula (III) in which Z' is a radical as defined above. Similarly, the compound (XI) obtained when reacting a compound of the above formula (X) with 1,4-diaminobenzene-2-sulfonic acid can react (rather than with another portion of the compound of formula (X)) with any unreacted 1,4-diaminobenzene-2-sulfonic acid to give a compound of the above formula (II) wherein Z a radical of the above formula (c), or in the ultimate treatment with an amine H—Z give a compound of the above formula (II) wherein Z is a radical of formula (d) or a radical as defined above. Thus, when a) reacting a compound of the above formula (IX) with about one equivalent of 2,4,6-trichlorotriazine;
b) reacting the compound of the above formula (X) thus obtained with 1,4-diaminobenzene-2-sulfonic acid;
c) reacting the compound of the above formula (XI) thus obtained with another portion of the compound of the above formula (X); and
d) reacting the product thus obtained with an amine;

there is obtained a mixture as defined hereinabove comprising a) a compound of the above formula (Ia) wherein $R_3'$ is a divalent radical of the above formula (a) and $R_2'$ is —$NH_2$ and Z as defined above;
b) a compound of the above formula (Ia) wherein $R_3'$ is —NH— and $R_2'$ is a radical of the above formula (b) and Z as defined above;
c) a compound of the above formula (II) wherein Z' is a radical of the above formula (c) and all the other substituents have the same meanings as defined above;
d) a compound of the above formula (II) wherein Z' is a radical of an amine, preferably a radical of formula (d) and all the other substituents have the same meanings as defined above and
e) a compound of the above formula (III) wherein Z' is a radical of an amine, or salts of these compounds.

If desired, a mixture of compounds thus obtained can be converted into a mixture of corresponding salts and, similarly, a mixture of salts thus obtained can be converted into a mixture of the corresponding compounds or into a mixture of other salts.

It will be appreciated that the relative quantities of the components of the mixture will depend on, inter alia, the exact reaction conditions used when preparing this mixture. In general, however, these relative quantities are approximately as follows:

Component a): 30–40%;
Component b): 30–47%;
Component c): 1.5–8%;
Component d): 2–11%; and
Component e): 12.5–23.5%.

Suitable amines H—Z' are ammonia and aliphatic amines, preferably substituted with a hydroxy, carboxy, alkoxy and/or sulphonic acid group, e.g. ethanolamine, diethanolamine, isopropanolamine, diisopropanolamine, 2-amino-hydroxypropane, glycine, N-methyl-ethanolamine, 3-methoxy-propylamine, 1-aminoethyl-2-sulfonic acid and most preferably, 1-methylamino-ethyl-2-sulfonic acid; aromatic amines, preferably substituted with a carboxy or sulphonic acid group, e.g. aniline, 4- or 3-sulpho-aniline, 4- or 3-carboxy-aniline; and heterocyclic amines, e.g. morpholine, piperazine or hydroxyethylpiperazine; or N,N-diethylaminopropylamine and 1,2-diaminopropane.

Suitable amines H—Z are the same as for H—Z' except the aromatic amines, with the proviso, that very reactive aromatic amines are suitable.

The compound of formula (IX), 3,10-diamino-6,13-dichloro-4,11-triphendioxazine disulphonic acid, is known. For the reaction with the 2,4,6-trichlorotriazine, the compound of formula (IX) is conveniently taken up in water, and the pH is brought to about 8.0–8.5 by addition of caustic alkali, preferably an aqueous lithium hydroxide solution. The 2,4,6-trichlorotriazine is conveniently utilized in the form of an aqueous suspension containing a small amount of a conventional surfactant, which is slowly added, under cooling to a temperature of about 0–10° C., preferably about 5–8° C., to the aqueous solution of the compound of formula (IX) under stirring, the pH of the reaction mixture being kept at about 8.0–8.5 by continuous addition of further caustic alkali, preferably aqueous lithium hydroxide solution, and the temperature being kept at about 0–10° C., preferably at about 5–8° C. Normally, the reaction is finished after about one hour. There is thus obtained an aqueous suspension of the compound of formula (X).

Conveniently about one half of the above suspension of the compound of formula (X) thus obtained is then reacted with 1,4-diaminobenzene-2-sulfonic acid giving compound (XI) (the second half of this suspension being kept for subsequent reaction with compound (XI)). The 1,4-diaminobenzene-2-sulfonic acid is conveniently suspended in water at a temperature about 35–45° C., preferably about 38–42° C., whereupon caustic alkali is added, preferably an aqueous lithium hydroxide solution, until the pH reaches a value of about 8 and solution takes place. This solution is then added to the aforesaid suspension of the compound of formula (X) at a temperature of about 40–55° C., preferably about 45–50° C., and after this addition the pH, which has reached a value of about 5.5–6, is kept at this value by addition of caustic alkali, preferably aqueous lithium hydroxide solution. Normally, the reaction is finished after about 4–5 hours.

The second half of the aforesaid suspension of the compound of formula (X) is then given to the suspension obtained in the foregoing operation, conveniently at a temperature of about 40° C., whereby the pH raises to about 6–7. The mixture is then heated, conveniently to a temperature of about 65–80° C., preferably about 72–75° C., which results in a decrease of the pH to about 5.5–6 at which value the pH is kept by addition of caustic alkali, preferably aqueous lithium hydroxide solution. In normal circumstances the reaction is finished after about 5–6 hours.

The suspension obtained in the foregoing operation is treated with 1-methylamino-ethyl-2-sulfonic acid which is conveniently utilized in the form of an aqueous solution of its sodium salt, or any other amine. This solution is added to the aforesaid suspension at a temperature of about 80–90° C., preferably about 82–86° C., whereby the pH rises from about 5 to about 10 and is then brought to and kept at about 8.2–8.6, preferably about 8.4, by addition of caustic alkali, preferably aqueous lithium hydroxide solution. The reaction is completed after 4–5 hours.

The resulting solution contains a mixture of compounds of formulae (I), (II) and (III), as defined hereinabove, in the form of alkali metal salts, preferably salts with lithium and sodium. This solution can be purified by conventional procedures, e.g. by filtration and/or ultrafiltration, and concentrated. If desired, the salts can be converted into the corresponding compounds of formulae (I), (II) and (III) or into other salts according to methods which are readily available to those skilled in the art. Conversely, compounds of formulae (I), (II) and (III) which may have been obtained by carrying out the synthesis described hereinabove in a slightly different manner, can be converted into salts. Suitable salts include the aforementioned lithium and sodium salts as well as potassium salts, ammonium salts etc. and inner salts.

The compounds according to the invention or their salts may be used for dyeing cationic dyeable materials such as: homo- or mixed-polymers of acrylonitrile, acid modified polyester or polyamide; wool; leather including low affinity vegetable-tanned leather; cotton; bast fibers such as hemp, flax, sisal, jute, coir and straw; regenerated cellulose fibers, glass or glass products comprising glass fibers; and substrates comprising cellulose for example paper and cotton. They may also be used for printing fibers, filaments and textiles comprising any of the above mentioned materials in accordance with known methods. Printing may be effected by impregnation of the material to be printed with a suitable printing paste comprising one or more compounds of the present invention. The type of printing paste employed, may vary depending on the material to be printed. Choice of a suitable commercially available printing paste or production of a suitable paste, is routine for one skilled in the art. Alternatively the compounds of the present invention may be used in the preparation of inks suitable for example for jet printing, in accordance with conventional methods.

Most preferably, the dyestuffs are used for dyeing or printing of paper e.g., sized or unsized, wood-free or wood-containing paper or paper-based products such as cardboard. They may be used in continuous dyeing in the stock, dyeing in the size press, in a conventional dipping or surface coloring process. The dyeing and printing of paper is effected by known methods.

The dyeings and prints and particularly those obtained on paper, show good fastness properties.

The compounds of formula (I) may be converted into dyeing preparations. Processing into stable liquid, preferably aqueous, or solid (granulated or powder form) dyeing preparations may take place in a generally known manner. Advantageously suitable liquid dyeing preparations may be made by dissolving the dyestuff or its salt in suitable solvents such as formamide, dimethylformamide, urea, glycols and ethers thereof, dextrin or addition products of boric acid with sorbitol which may be used together with water, optionally adding an assistant, e:g. a stabilizer. Such preparations may be obtained, for example, as described in French patent specification No. 1,572,030.

The compounds of formula (I) (in the corresponding salt form) have good solubility especially in cold water. Owing to their high substantivity the compounds of the present invention exhaust practically quantitatively and show a good build-up power. They can be added to the stock directly, i.e. without previously dissolving, as either a dry powder or granulate, without reducing the brilliance or the yield of color. They can also be used in soft water without loss of yield. They do not mottle when applied on paper, are not inclined to give two-sided dyeing on paper and are practically insensitive to filler or pH variations. They operate over a broad pH range, in the range of from pH 3 to 10. When producing sized or unsized paper, the waste water is essentially colorless. This feature, which is extremely important from an environmental view-point, when compared with similar known dyes, shows a marked improvement. A sized paper dyeing when compared with the corresponding unsized paper dyeing does not show any decrease in strength.

The paper dyeings or printings made with the compounds, in particular the metal-free forms, according to the invention are clear and brilliant and have very good light fastness: On exposure to light for a long time, the shade of the dyeing fades tone in tone. They show very good wet fastness properties; being fast to water, milk, fruit juice, sweetened mineral water, tonic water, soap and sodium chloride solution, urine etc. Furthermore, they have good alcohol fastness properties. The wet fastness properties are improved compared to known dyes showing otherwise similar properties. They do not exhibit a tendency towards two-sidedness.

Paper dyed or printed with the compounds of the present invention can be bleached oxidatively, a feature which is important for the recycling of waste and old paper/paper products. This property, together with the improved backwater results and wet-fastness, shows a marked improvement over known dyes having otherwise similar properties.

The compounds of the present invention may also be used to dye paper containing wood-pulp where even dyeings, having good fastness properties are obtained. Furthermore, they may be used for the production of coated paper in accordance with known methods. Preferably when coating, a suitable filler, for example kaolin, is employed in order to give a one-side coated paper.

The compounds of the present invention are also suitable for dyeing in combination with other dyes for example other cationic or anionic dyes. The compatibility of the compounds of the present invention when used as a dye in mixtures with other commercially available dyes, may be determined according to conventional methods. The thus obtained dyeings have good fastness properties.

The compounds of the present invention are also suitable for the preparation of ink jet inks.

The invention further provides a substrate which has been dyed or printed with a compound of the present invention. The substrate may be selected from any of the above mentioned substrates. A preferred substrate is a substrate comprising cellulose such as cotton or paper or a paper based product. The most preferred substrate is paper or a paper based product.

The following Examples further serve to illustrate the present invention. In these Examples all parts and all the percentages are by weight or volume, and the temperatures given are in degrees Celsius, unless indicated to the contrary.

EXAMPLE 1 a) Preparation of Intermediate A 13 parts of the compound with the formula

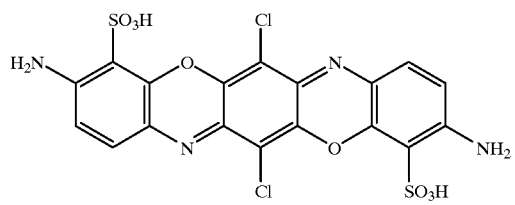

are dissolved in 220 parts water and brought to pH 8–8.5 with lithium hydroxide. 50 parts of ice are added, the solution is divided in two equal parts and kept at 4° C. 2.4 parts of 2,4,6-trichloro-s-triazine are dispersed in 10 parts water and 5 parts ice as well as a dispersing agent are added. The suspension is stirred for 30 minutes and added portion wise to the first part of the solution of the dioxazine compound whereby the pH value is kept at 8–8.5 with lithium hydroxide and the temperature at 4–7° C. Then the mixture is stirred for 2 hours and the pH is lowered to 5.5–6 with acid. After addition of the second part of the dioxazine solution, the mixture is heated to 70–75° C. The reaction is finished after 6 hours. 14.3 parts of a compound with the formula

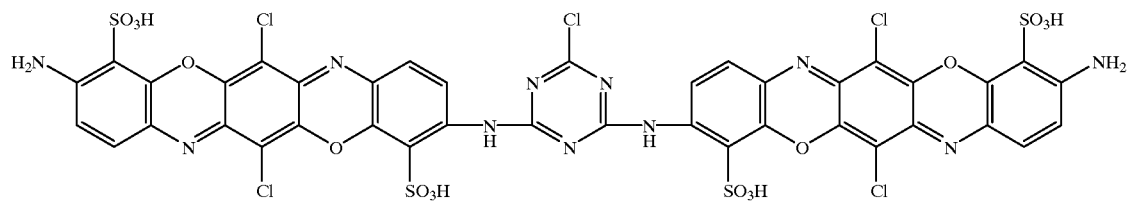

(intermediate A) in 312 parts of water is obtained in the form of the lithium salt.

b) Reduction of Intermediate A 14.3 parts of the intermediate A in 312 parts of water are put into a reaction vessel and 128.4 parts hydrochloric acid are added under nitrogen atmosphere while stirring vigorously. The mixture is stirred for a further 30 minute and 1.34 parts iron powder are added within 3–4 hours. The reaction continues over night and the brown suspension is filtered. 14.4 parts of the reduced intermediate A (corresponding to formula (II) in which X is Cl and $R_4$ and $R_6$ are H) are obtained.

c) Preparation of Intermediate B 7.1 parts 1-amino-benzene-2-sulfonic acid are dissolved in 110 parts water and neutralized (pH 7–7.5) with lithium hydroxide. 8 parts of 2,4,6-trichlorotriazine are dispersed in 40 parts ice water and dispersing agent by stirring during 30 minutes. The suspension is added to the solution of the aminobenzenesulphonic acid salt portionwise within 1 hour at 4–7° C. and at pH 4.8–5.2. The mixture is stirred over night at 0–5° C. 13.2 parts of the compound with the formula

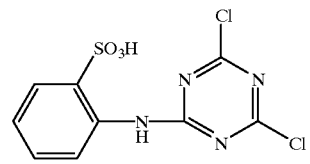

(intermediate B) in 227 parts of water are obtained in the form of the lithium salt.

d) Condensation of Reduced Intermediate A with Intermediate B 14.4 parts of the reduced intermediate A are stirred under nitrogen atmosphere into 240 parts water. The reaction mixture from step c) is added at once and the pH adjusted to a value 4 within 10–15 minutes. The mixture is then heated to 60° C. and stirred for 16 hours at pH 4 and 60° C. The temperature is raised to 70° C. and the reaction continued for about 1.5 hours. 21.1 parts of the compound with the formula

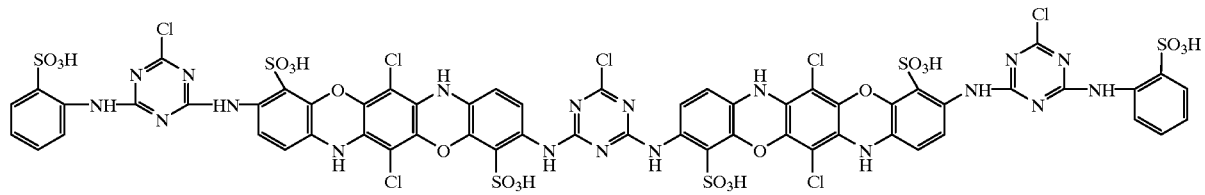

(intermediate C) in 619 parts of water as a colloidal solution are obtained.

e) Condensation of Intermediate C with 1-methyl-aminoethyl-2-sulfonic Acid 640 parts of the colloidal solution obtained in step d) are put into a reaction vessel and 10 parts 1-methylamino-ethyl-2-sulfonic acid in the form of the sodium salt as a solution is added. The mixture is heated to 80° C. and left during 1 hour and over night at 80° C. and pH 8 (if necessary, by addition of lithium hydroxide) with normal air present. At the same time as the condensation takes place, the leuco form is oxidized and the dyestuff is precipitated with sodium chloride, filtered and dried at 60° C. in vacuum. 24.8 parts of the blue dyestuff with the formula 640 parts of the colloidal solution of step d) are put into a reaction vessel and 6 parts of diethanolamine are added. The mixture is heated to 80–85° C. and left over night at 80–85° C. and pH 8 (if necessary by addition of lithiumhydroxide) with normal air present. At the same time as the condensation takes place, the leuco form is oxidized. The reaction mixture is cooled to 50° C. and filtered. 650 parts process solution are ultrafiltrated at 40–50° C. using a suitable membrane (e.g. G10; G20; G50) and concentrated up to 400 parts solution. The obtained liquid dyestuff formulation contains only traces of the remaining inorganic salts and exhibits perfect storage stability. $\lambda_{max}$ is 555.7 nm (in water and 1% acetate).

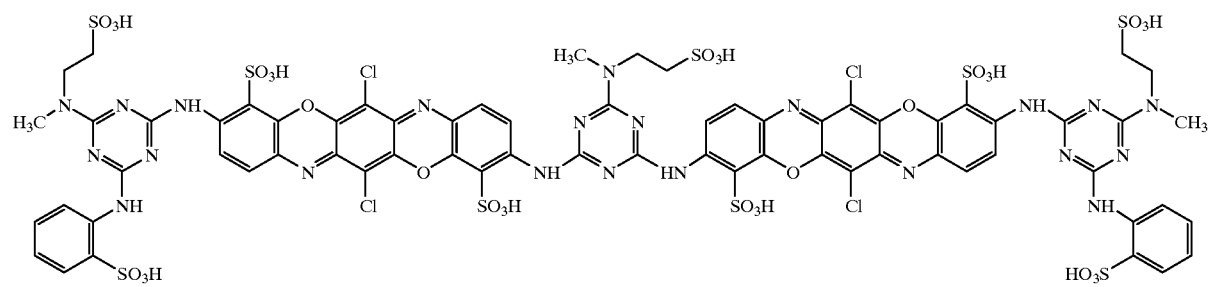

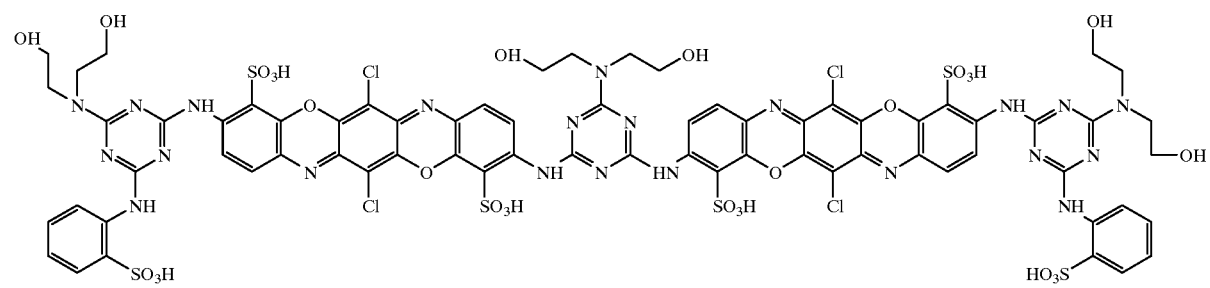

is obtained in the mixed lithium/sodium salt form. $\lambda_{max}$ is 564.4 nm (in water and 1% acetate).

EXAMPLE 2

Following the procedure of Example 1 the condensation of intermediate C was performed with diethanolamine.

EXAMPLES 3–84

Following the procedure of Example 1 or an analogous procedure with similar reactants, further dyestuffs according to formula (Ic)

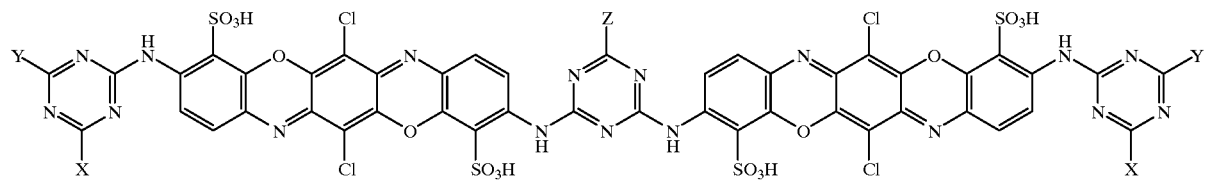

(Ic)

can be obtained which are illustrated in the following Table 1.

TABLE 1

Examples 3–84

| Ex. | H—X | H—Y | H—Z | $\lambda_{max}$* |
|---|---|---|---|---|
| 3 | 2-aminobenzenesulfonic acid | H₂N-CH₂CH₂-OH | H₂N-CH₂CH₂-OH | 558.1 nm |
| 4 | " | H₃C-NH-CH₂CH₂-OH | H₃C-NH-CH₂CH₂-OH | 556.8 nm |
| 5 | " | H₂N-CH₂CH₂CH₂-O-CH₃ | H₂N-CH₂CH₂CH₂-O-CH₃ | 558.3 nm |
| 6 | " | morpholine | morpholine | 557.7 nm |
| 7 | " | H₂N-CH₂CH₂-SO₃H | H₂N-CH₂CH₂-SO₃H | 562.3 nm |
| 8 | 3-aminobenzenesulfonic acid | H₂N-CH₂CH₂-OH | H₂N-CH₂CH₂-OH | 556.8 nm |
| 9 | " | H₃C-NH-CH₂CH₂-OH | H₃C-NH-CH₂CH₂-OH | 556.2 nm |
| 10 | " | H₂N-CH₂CH₂CH₂-O-CH₃ | H₂N-CH₂CH₂CH₂-O-CH₃ | 557.0 nm |
| 11 | " | HO-CH₂CH₂-NH-CH₂CH₂-OH | HO-CH₂CH₂-NH-CH₂CH₂-OH | 557.3 nm |
| 12 | " | morpholine | morpholine | 558.3 nm |
| 13 | " | H₂N-CH₂CH₂-SO₃H | H₂N-CH₂CH₂-SO₃H | 561.1 nm |
| 14 | " | H₃C-NH-CH₂CH₂-SO₃H | H₃C-NH-CH₂CH₂-SO₃H | 560.1 nm |

TABLE 1-continued

Examples 3–84

| Ex. | H—X | H—Y | H—Z | $\lambda_{max}$* |
|---|---|---|---|---|
| 15 | 4-HO₃S-C₆H₄-NH₂ | H₂N-CH₂CH₂-OH | H₂N-CH₂CH₂-OH | 561.9 nm |
| 16 | " | H₃C-NH-CH₂CH₂-OH | H₃C-NH-CH₂CH₂-OH | 560.7 nm |
| 17 | " | H₂N-CH₂CH₂CH₂-O-CH₃ | H₂N-CH₂CH₂CH₂-O-CH₃ | 560.3 nm |
| 18 | " | HO-CH₂CH₂-NH-CH₂CH₂-OH | HO-CH₂CH₂-NH-CH₂CH₂-OH | 562.9 nm |
| 19 | " | " | H₂N-CH₂CH₂CH₂-N(CH₂CH₃)(CH₃) (diethylamino propyl) | 556.5 nm |
| 20 | " | morpholine (HN-CH₂CH₂-O-CH₂CH₂-) | morpholine | 555.4 nm |
| 21 | " | H₂N-CH₂CH₂-SO₃H | H₂N-CH₂CH₂-SO₃H | 560.2 nm |
| 22 | " | H₃C-NH-CH₂CH₂-SO₃H | H₃C-NH-CH₂CH₂-SO₃H | 559.7 nm |
| 23 | 1-SO₃H-2-NH₂-naphthalene | H₂N-CH₂CH₂-OH | H₂N-CH₂CH₂-OH | 550.3 nm |
| 24 | " | H₃C-NH-CH₂CH₂-OH | H₃C-NH-CH₂CH₂-OH | 551.1 nm |
| 25 | " | HO-CH₂CH₂-NH-CH₂CH₂-OH | HO-CH₂CH₂-NH-CH₂CH₂-OH | 549.4 nm |
| 26 | " | " | H₃C-NH-CH₂CH₂-SO₃H | 553.7 nm |
| 27 | " | H₂N-CH₂CH₂-SO₃H | H₂N-CH₂CH₂-SO₃H | 560.9 nm |
| 28 | " | H₃C-NH-CH₂CH₂-SO₃H | H₃C-NH-CH₂CH₂-SO₃H | 562.2 nm |
| 29 | 6-NH₂-2-HO₃S-naphthalene | H₂N-CH₂CH₂-OH | H₂N-CH₂CH₂-OH | 564.2 nm |
| 30 | " | HO-CH₂CH₂-NH-CH₂CH₂-OH | HO-CH₂CH₂-NH-CH₂CH₂-OH | 566.0 nm |

TABLE 1-continued

Examples 3–84

| Ex. | H—X | H—Y | H—Z | $\lambda_{max}$* |
|---|---|---|---|---|
| 31 | " | " | H₃C-NH-CH₂CH₂-SO₃H | 571.8 nm |
| 32 | " | H₂N-CH₂CH₂-SO₃H | H₂N-CH₂CH₂-SO₃H | 574.9 nm |
| 33 | " | H₃C-NH-CH₂CH₂-SO₃H | H₃C-NH-CH₂CH₂-SO₃H | 575.2 nm |
| 34 | 2-amino benzoic acid (NH₂, COOH on benzene) | H₂N-CH₂CH₂-OH | H₂N-CH₂CH₂-OH | 550.0 nm |
| 35 | " | H₃C-NH-CH₂CH₂-OH | H₃C-NH-CH₂CH₂-OH | 552.4 nm |
| 36 | " | H₂N-CH₂CH₂CH₂-O-CH₃ | H₂N-CH₂CH₂CH₂-O-CH₃ | 557.3 nm |
| 37 | " | HO-CH₂CH₂-NH-CH₂CH₂-OH | HO-CH₂CH₂-NH-CH₂CH₂-OH | 550.1 nm |
| 38 | " | " | H₂N-CH₂CH₂CH₂-N(CH₂CH₃)₂ | 559.0 nm |
| 39 | " | H₂N-CH₂CH₂-SO₃H | H₂N-CH₂CH₂-SO₃H | 563.7 nm |
| 40 | " | H₃C-NH-CH₂CH₂-SO₃H | H₃C-NH-CH₂CH₂-SO₃H | 568.6 nm |
| 41 | " | " | H₂N-CH₂CH₂CH₂-N(CH₂CH₃)₂ | 564.5 nm |
| 42 | 3-amino benzoic acid (NH₂, COOH on benzene) | H₂N-CH₂CH₂-OH | H₂N-CH₂CH₂-OH | 561.2 nm |
| 43 | " | H₃C-NH-CH₂CH₂-OH | H₃C-NH-CH₂CH₂-OH | 562.4 nm |
| 44 | " | H₂N-CH₂CH₂CH₂-O-CH₃ | H₂N-CH₂CH₂CH₂-O-CH₃ | 561.7 nm |
| 45 | " | HO-CH₂CH₂-NH-CH₂CH₂-OH | HO-CH₂CH₂-NH-CH₂CH₂-OH | 561.4 nm |
| 46 | " | H₂N-CH₂CH₂-SO₃H | H₂N-CH₂CH₂-SO₃H | 563.8 nm |

TABLE 1-continued

Examples 3–84

| Ex. | H—X | H—Y | H—Z | $\lambda_{max}$* |
|---|---|---|---|---|
| 47 | " | H₃C-NH-CH₂CH₂-SO₃H | H₃C-NH-CH₂CH₂-SO₃H | 564.9 nm |
| 48 | " | " | H₂N-CH₂CH₂CH₂-N(C₂H₅)₂ | 562.6 nm |
| 49 | 4-aminobenzoic acid (COOH / NH₂) | H₂N-CH₂CH₂-OH | H₂N-CH₂CH₂-OH | 572.9 nm |
| 50 | " | H₃C-NH-CH₂CH₂-OH | H₃C-NH-CH₂CH₂-OH | 573.6 nm |
| 51 | " | H₂N-CH₂CH₂CH₂-O-CH₃ | H₂N-CH₂CH₂CH₂-O-CH₃ | 572.7 nm |
| 52 | " | HO-CH₂CH₂-NH-CH₂CH₂-OH | HO-CH₂CH₂-NH-CH₂CH₂-OH | 575.3 nm |
| 53 | " | H₂N-CH₂CH₂-SO₃H | H₂N-CH₂CH₂-SO₃H | 566.4 nm |
| 54 | " | H₃C-NH-CH₂CH₂-SO₃H | H₃C-NH-CH₂CH₂-SO₃H | 563.6 nm |
| 55 | 3-amino-4-methoxybenzoic acid | H₂N-CH₂CH₂-OH | H₂N-CH₂CH₂-OH | 559.4 nm |
| 56 | " | H₃C-NH-CH₂CH₂-OH | H₃C-NH-CH₂CH₂-OH | 560.1 nm |
| 57 | " | HO-CH₂CH₂-NH-CH₂CH₂-OH | HO-CH₂CH₂-NH-CH₂CH₂-OH | 560.0 nm |
| 58 | " | " | H₂N-CH₂CH₂CH₂-N(C₂H₅)₂ | 570.1 nm |
| 59 | " | morpholine | morpholine | 561.8 nm |
| 60 | " | H₂N-CH₂CH₂-SO₃H | H₂N-CH₂CH₂-SO₃H | 562.2 nm |
| 61 | " | H₃C-NH-CH₂CH₂-SO₃H | H₃C-NH-CH₂CH₂-SO₃H | 562.3 nm |

TABLE 1-continued

Examples 3–84

| Ex. | H—X | H—Y | H—Z | $\lambda_{max}$* |
|---|---|---|---|---|
| 62 | 2-amino-5-methylbenzenesulfonic acid (HO₃S, H₂N, CH₃ on benzene) | H₂N-CH₂CH₂-OH | H₂N-CH₂CH₂-OH | 554.9 nm |
| 63 | " | H₃C-NH-CH₂CH₂-OH | H₃C-NH-CH₂CH₂-OH | 555.5 nm |
| 64 | " | HO-CH₂CH₂-NH-CH₂CH₂-OH | HO-CH₂CH₂-NH-CH₂CH₂-OH | 556.5 nm |
| 65 | " | morpholine (HN-O ring) | morpholine (HN-O ring) | 556.2 nm |
| 66 | " | H₂N-CH₂CH₂-SO₃H | H₂N-CH₂CH₂-SO₃H | 562.0 nm |
| 67 | " | H₃C-NH-CH₂CH₂-SO₃H | H₃C-NH-CH₂CH₂-SO₃H | 562.5 nm |
| 68 | 4-amino-3-methylbenzenesulfonic acid (NH₂, CH₃, HO₃S on benzene) | H₂N-CH₂CH₂-OH | H₂N-CH₂CH₂-OH | 540.3 nm |
| 69 | " | H₃C-NH-CH₂CH₂-OH | H₃C-NH-CH₂CH₂-OH | 540.1 nm |
| 70 | " | HO-CH₂CH₂-NH-CH₂CH₂-OH | HO-CH₂CH₂-NH-CH₂CH₂-OH | 539.9 nm |
| 71 | " | H₂N-CH₂CH₂-SO₃H | H₂N-CH₂CH₂-SO₃H | 561.7 nm |
| 72 | " | H₃C-NH-CH₂CH₂-SO₃H | H₃C-NH-CH₂CH₂-SO₃H | 562.7 nm |
| 73 | 2-amino-5-methoxybenzenesulfonic acid (SO₃H, H₃CO, NH₂ on benzene) | H₂N-CH₂CH₂-OH | H₂N-CH₂CH₂-OH | 553.7 nm |
| 74 | " | H₃C-NH-CH₂CH₂-OH | H₃C-NH-CH₂CH₂-OH | 553.9 nm |
| 75 | " | HO-CH₂CH₂-NH-CH₂CH₂-OH | HO-CH₂CH₂-NH-CH₂CH₂-OH | 554.2 nm |
| 76 | " | morpholine (HN-O ring) | morpholine (HN-O ring) | 555.4 nm |

TABLE 1-continued

Examples 3–84

| Ex. | H—X | H—Y | H—Z | $\lambda_{max}$* |
|---|---|---|---|---|
| 77 | " | H₂N−CH₂CH₂−SO₃H | H₂N−CH₂CH₂−SO₃H | 557.2 nm |
| 78 | H₂N−CH₂CH₂−OH | HO−CH₂CH₂−NH−CH₂CH₂−OH | HO−CH₂CH₂−NH−CH₂CH₂−OH | 561.9 nm |
| 79 | " | H₃C−NH−CH₂CH₂−SO₃H | " | 558.7 nm |
| 80 | " | " | H₃C−NH−CH₂CH₂−SO₃H | 545.7 nm |
| 81 | HO−CH₂CH₂−NH−CH₂CH₂−OH | HO−CH₂CH₂−NH−CH₂CH₂−OH | " | 561.2 nm |
| 82 | H₂N−(CH₂)₃−N(CH₂CH₃)(CH₂CH₃) | H₂N−(CH₂)₃−N(CH₂CH₃)(CH₂CH₃) | H₂N−(CH₂)₃−N(CH₂CH₃)(CH₂CH₃) | 606.6 nm |
| 83 | " | 3-amino-benzoic acid (m-H₂N-C₆H₄-COOH) with NH₂ | H₂N−(CH₂)₃−N(CH₂CH₃)(CH₂CH₃) | 571.7 nm |
| 84 | H₂N−CH(CH₃)−CH₂−NH₂ | H₂N−CH(CH₃)−CH₂−NH₂ | H₂N−CH(CH₃)−CH₂−NH₂ | 611.4 nm |

*All examples measured in water + 1% acetate; except: examples 82) and 84) measured in DIF + 1% acetic acid.

All these dyestuffs dye cotton or paper in brilliant reddish blue or blue shades with excellent fastnesses.

EXAMPLE 85 a) 82.0 parts of 3,10-diamino-6,13-dichloro-4,11-triphendioxazine disulphonic acid are added, with stirring and at 20–25° C., to 750 parts of water. At the same temperature a solution of 16.5 parts of lithium hydroxide monohydrate, in the form of 100 parts of a 4 N solution, is added over 2–3 hours at pH 8–8.5. 1100 parts of a solution are obtained.

b) 30.4 parts of 2,4,6-trichlorotriazine are added in portions, with stirring and at 1–4° C., to a mixture of 67 parts of water, 0.3 parts of a conventional surfactant and 22 parts of ice. Stirring is continued for 5 minutes, the temperature is kept at 1–4° C. by addition of further 37 parts of ice, and stirring is continued for further 15 minutes. 150 parts of a assuspension are obtained.

c) The solution obtained in a) is brought to a temperature of 5–8° C. by addition of 240 parts of ice. The suspension obtained in b) is added with stirring over 2 hours, the pH is maintained at 8.0–8.3 by continuous addition of 4 N lithium hydroxide solution, and the temperature is kept at 5–8° C. by adding 75 parts of ice portion-wise. Stirring is continued for one hour at the same pH range, and the temperature rises to 10–12° C. The volume of the resulting suspension is about 1700 parts.

d) 15.5 parts of 1,4-diaminobenzene-2-sulfonic acid are suspended in 200 parts of water. The pH is about 3. The suspension is heated to 40° C., and the pH is brought to 8 by addition of 4 N lithium hydroxide solution. 230 parts of a dark-brown solution are obtained.

e) One half (about 850 parts) of the suspension obtained in c) is heated to about 45° C., the pH decreases to 6–7. The solution obtained in d) is added, whereby the pH starts to decrease further. When the pH reaches 5.5–6, it is kept at that value by addition of 4 N lithium hydroxide solution. The mixture is heated to 50° and kept at this temperature until the reaction is complete (about 4 hours). 1150 parts of a suspension are obtained.

f) The second half of the suspension obtained in c) is heated to 40° C., the pH is decreased to 6–7, and added to the suspension obtained in e). The vessel in which the suspension obtained in c) had been prepared is rinsed with 200 parts of water, and the rinsings are added to the mixture. The pH rises to 6–6.5, the mixture is heated to 70–72° C., the pH decreases again to 5.5–6 and is kept at that value by addition of 4 N lithium hydroxide solution. After 5–6 hours at 72–75° C. the reaction is complete. 2200 parts of a suspension are obtained.

g) 75 parts of 1-methylamino-ethyl-2-sulfonic acid, in the form of a 39% aqueous solution of its sodium salt are added to the suspension obtained in f). The pH rises from 5 to 10. The temperature is kept at 84° C. (+/−2° C.), and the pH is kept at 8.4 (+/−0.2) by addition of 4 N lithium hydroxide solution. After about 4–5 hours the reaction is complete. 2350 parts of a solution are obtained.

h) 16 parts of a conventional filtration aid are added to the solution obtained in g). After stirring for about 20 minutes the suspension is filtered by suction. The filtrate is subjected, at 48–50° C., to ultrafiltration using an appropriate conventional membrane and 9500 parts of demineralised water and thereafter concentrated to a volume of 2000 parts. The resulting stable dark-blue solution contains about 6% of dyestuffs, namely a mixture of about a) 30–40% of the following compound

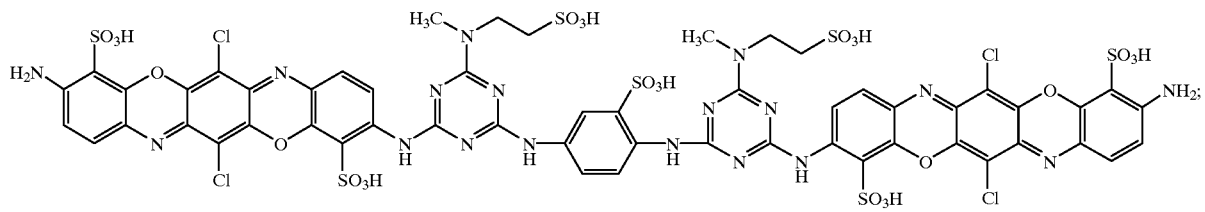

b) 30–47% of the following compound

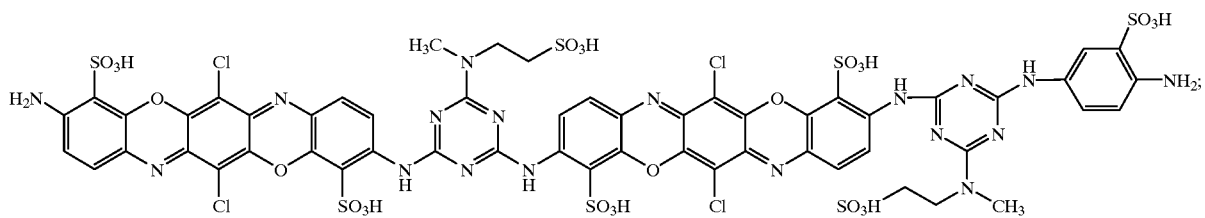

c) 1.5–8% of the following compound

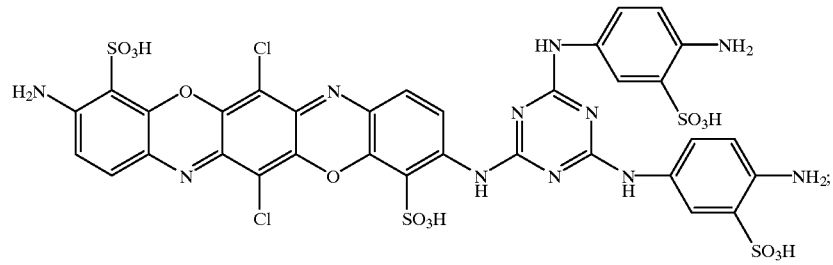

d) 2–11% of the following compound

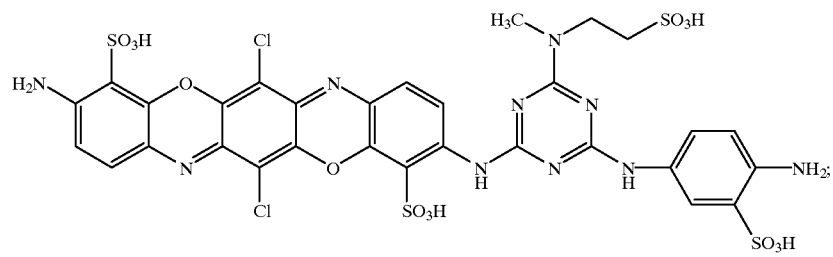

and e) 12.5–23.5% of the following compound

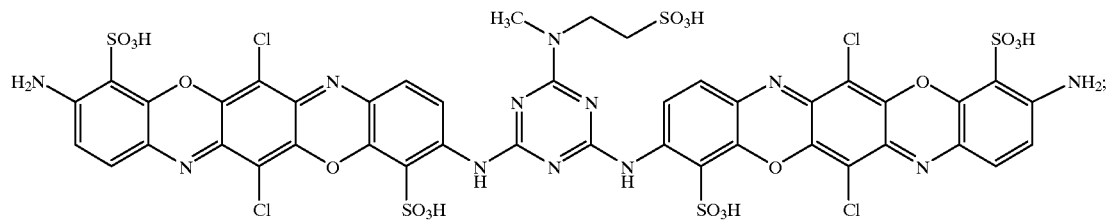

in the form of their lithium/sodium salts, corresponding to about 5.5% of the free acids. The $\lambda_{max}$ value is 572.1 nm (in water and 1% acetate).

EXAMPLE 86

The steps a)–f) are analogous to Example 85.

In step g) instead of using 75 parts of 1-methylamino-ethyl-2-sulfonic acid solution 22.5 parts of 1-amino-ethyl-2-sulfonic acid in 50 parts water are used under the same condition as mentioned in step g).

After 4–5 hours the reaction is complete. The dyestuff is precipitated with sodium chloride, filtered and dried at 60° C. in vacuum. 130 parts of the dyestuff are obtained. $\lambda_{max}$ is 571.5 nm (in water and 1% acetate).

TABLE 2

Examples 87–134
In analogy to the Example 85 further dyestuffs can be obtained. But instead of using 1-methylamino-ethyl-2-sulfonic acid as in Example 85 step g) the following substances H—Z as illustrated in Table 2 are used. Further analogously or instead as in step d) the following compounds S are used in the corresponding molar amount.

| Ex | S | H—Z | $\lambda_{max}$* |
|---|---|---|---|
| 87 | H₂N–C₆H₃(SO₃H)–NH₂ | H₂N–CH₂CH₂–OH | 572.5 nm |
| 88 | " | HO–CH₂CH₂–NH–CH₂CH₂–OH | 572.7 nm |
| 89 | " | H₃C–NH–CH₂CH₂–OH | 570.5 nm |
| 90 | " | H₂N–CH₂CH₂CH₂–O–CH₃ | 571.4 nm |
| 91 | " | morpholine (HN–O) | 566.0 nm |
| 92 | H₂N–C₆H₃(SO₃H)(NH₂) | H₂N–CH₂CH₂–OH | 570.3 nm |
| 93 | " | HO–CH₂CH₂–NH–CH₂CH₂–OH | 570.5 nm |
| 94 | " | H₃C–NH–CH₂CH₂–OH | 570.1 nm |

TABLE 2-continued

Examples 87–134

In analogy to the Example 85 further dyestuffs can be obtained. But instead of using 1-methylamino-ethyl-2-sulfonic acid as in Example 85 step g) the following substances H—Z as illustrated in Table 2 are used. Further analogously or instead as in step d) the following compounds S are used in the corresponding molar amount.

| Ex | S | H—Z | $\lambda_{max}$* |
|---|---|---|---|
| 95 | " | 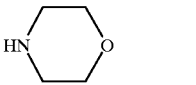 | 565.7 nm |
| 96 | " | 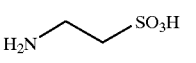 | 569.3 nm |
| 97 | " | 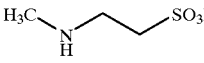 | 569.8 nm |
| 98 | 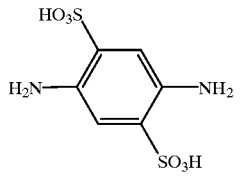 | 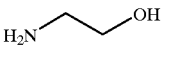 | 574.7 nm |
| 99 | " | 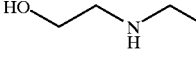 | 575.6 nm |
| 100 | " | 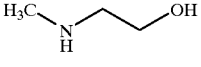 | 573.9 nm |
| 101 | " | 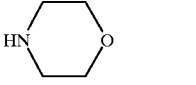 | 574.2 nm |
| 102 | " | 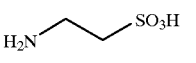 | 577.7 nm |
| 103 | " | 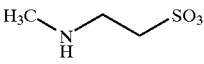 | 578.5 nm |
| 104 | 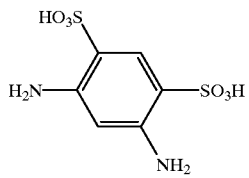 | 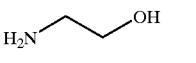 | 570.7 nm |
| 105 | " | 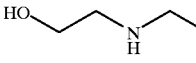 | 571.4 nm |
| 106 | " | 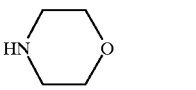 | 570.9 nm |
| 107 | " | 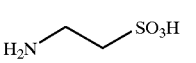 | 566.4 nm |
| 108 | " | 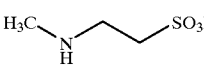 | 563.3 nm |

TABLE 2-continued

Examples 87–134
In analogy to the Example 85 further dyestuffs can be obtained. But instead of using
1-methylamino-ethyl-2-sulfonic acid as in Example 85 step g) the following substances
H—Z as illustrated in Table 2 are used. Further analogously or instead as in step d) the
following compounds S are used in the corresponding molar amount.

| Ex | S | H—Z | $\lambda_{max}$* |
|---|---|---|---|
| 109 | 3,5-diaminobenzoic acid (H₂N–C₆H₃(COOH)–NH₂) | H₂N–CH₂CH₂–OH | 569.4 nm |
| 110 | " | HO–CH₂CH₂–NH–CH₂CH₂–OH | 568.7 nm |
| 111 | " | morpholine (HN–CH₂CH₂–O–CH₂CH₂) | 568.1 nm |
| 112 | " | H₂N–CH₂CH₂–SO₃H | 571.4 nm |
| 113 | " | H₃C–NH–CH₂CH₂–SO₃H | 571.8 nm |
| 114 | p-phenylenediamine (H₂N–C₆H₄–NH₂) | H₂N–CH₂CH₂–OH | 592.7 nm |
| 115 | " | HO–CH₂CH₂–NH–CH₂CH₂–OH | 593.8 nm |
| 116 | " | H₂N–CH₂CH₂–SO₃H | 594.6 nm |
| 117 | " | H₃C–NH–CH₂CH₂–SO₃H | 595.1 nm |
| 118 | m-phenylenediamine (H₂N–C₆H₄–NH₂) | H₂N–CH₂CH₂–OH | 586.3 nm |
| 119 | " | H₃C–NH–CH₂CH₂–SO₃H | 580.7 nm |
| 120 | 4,4'-diaminostilbene-2,2'-disulfonic acid | H₂N–CH₂CH₂–OH | 576.4 nm |
| 121 | " | H₂N–CH₂CH₂–SO₃H | 577.9 nm |

TABLE 2-continued

Examples 87–134

In analogy to the Example 85 further dyestuffs can be obtained. But instead of using 1-methylamino-ethyl-2-sulfonic acid as in Example 85 step g) the following substances H—Z as illustrated in Table 2 are used. Further analogously or instead as in step d) the following compounds S are used in the corresponding molar amount.

| Ex | S | H—Z | $\lambda_{max}$* |
|---|---|---|---|
| 122 | " | $H_3C-NH-CH_2CH_2-SO_3H$ | 580.3 nm |
| 123 | $H_2N-C_6H_4-SO_2-C_6H_4-NH_2$ | $HO-CH_2CH_2-NH-CH_2CH_2-OH$ | 581.4 nm |
| 124 | " | $H_3C-NH-CH_2CH_2-SO_3H$ | 583.2 nm |
| 125 | 5,5'-(carbonyldiimino)bis[2-amino-phenol-4-sulfonic acid] | $HO-CH_2CH_2-NH-CH_2CH_2-OH$ | 561.0 nm |
| 126 | " | $H_3C-NH-CH_2CH_2-SO_3H$ | 563.7 nm |
| 127 | 4,4'-(carbonyldiimino)bis[2-sulfo-aniline] | $HO-CH_2CH_2-NH-CH_2CH_2-OH$ | 569.7 nm |
| 128 | " | $H_3C-NH-CH_2CH_2-SO_3H$ | 575.2 nm |
| 129 | 4,4'-diamino-biphenyl-2,2'-disulfonic acid | $HO-CH_2CH_2-NH-CH_2CH_2-OH$ | 571.1 nm |
| 130 | " | $H_3C-NH-CH_2CH_2-SO_3H$ | 571.6 nm |
| 131 | 4,4'-methylenebis[2-amino-benzenesulfonic acid] | $HO-CH_2CH_2-NH-CH_2CH_2-OH$ | 572.6 nm |
| 132 | " | $H_3C-NH-CH_2CH_2-SO_3H$ | 573.4 nm |

TABLE 2-continued

Examples 87–134
In analogy to the Example 85 further dyestuffs can be obtained. But instead of using
1-methylamino-ethyl-2-sulfonic acid as in Example 85 step g) the following substances
H—Z as illustrated in Table 2 are used. Further analogously or instead as in step d) the
following compounds S are used in the corresponding molar amount.

| Ex | S | H—Z | $\lambda_{max}$* |
|---|---|---|---|
| 133 | HOOC-C₆H₃(NH₂)-CH₂-C₆H₃(NH₂)-COOH | HO-CH₂CH₂-NH-CH₂CH₂-OH | 571.2 nm |
| 134 | " | H₃C-NH-CH₂CH₂-SO₃H | 564.7 nm |

*All examples measured in water + 1% acetate

The application of the dyestuffs is illustrated in the following Application Examples.

APPLICATION EXAMPLE A 70 parts of chemically bleached sulfite cellulose obtained from pinewood and 30 parts of chemically bleached cellulose obtained from birchwood are beaten in 2000 parts of water in a Hollander. 0.2 parts of the dyestuff solution obtained in step h) of Example 85 are sprinkled into this pulp. After mixing for 10 minutes, paper is produced from this pulp. The absorbent paper obtained in this way is dyed a brilliant blue. The waste water is colorless.

APPLICATION EXAMPLE B 0.2 parts of the dyestuff solution obtained in step h) of Example 85 are dissolved in 100 parts of water. This solution is added to 100 parts of chemically bleached sulfite cellulose which have been ground with 2000 parts of water in a Hollander. After mixing thoroughly for 15 minutes, resin size and aluminium sulfate are added thereto. Paper produced in this way has a brilliant blue nuance and exhibits perfect light and wet fastness.

APPLICATION EXAMPLE C

An absorbent length of unsized paper is drawn at 40–50° C. through a dyestuff solution having the following composition:

---
0.3 parts of the dyestuff solution obtained in step h) of Example 85;
0.5 parts of starch; and
99.0 parts of water.
---

The excess dyestuff solution is squeezed out trough two rollers. The dried length of paper is dyed a brilliant blue shade. The paper dyeing obtained shows good fastness properties.

The dyestuff of Examples 1–84 and 86–134 may also be used for dyeing by a method analogous to that of Application Examples A to C. The paper dyeings obtained show good fastness properties.

APPLICATION EXAMPLE D 2 parts of the dyestuff solution obtained in step h) of Example 85 are dissolved in 1000 parts of demineralised water at 40° C. 100 parts of a pre-wetted cotton textile substrate are added, and the bath is heated to the boiling point over 30 minutes and held at the boil for one hour. Any water which evaporates during dyeing is replaced continuously. The dyed substrate is removed from the bath and, after rinsing and drying, a brilliant blue dyeing is obtained which has good light- and wet-fastness properties. The dyestuff exhausts practically totally onto the fiber, and the waste water is almost colorless.

In a similar manner as described in Application Example D the dyestuffs according to Examples 1–84 and 86–134 may be used for dyeing cotton.

APPLICATION EXAMPLE E 100 parts freshly tanned and neutralized chrome leather are agitated for 30 minutes in a vessel with a liquor consisting of 250 parts of water at 55° C. and 0.5 parts of the dyestuff of Example 1 and then treated in the same bath for 30 minutes with 2 parts of an anionic fatty licker based on sulphonated train oil. The leather is then dried and prepared in the normal way, giving a leather evenly dyed in a brilliant blue shade.

By a method analogous to that described in Application Example E the dyestuffs according to Examples 2–134 may be used for dyeing leather.

Further vegetable-tanned leathers of low affinity may be dyed using the dyestuffs as described herein in accordance with known methods.

APPLICATION EXAMPLE F

Water is added to a dry pulp in a Hollander, said dry pulp consisting of 60% (by weight) of mechanical wood pulp and 40% (by weight) of unbleached sulfite cellulose, and the slurry is beaten in order to obtain a dry content slightly exceeding 2.5% and having a beating degree of 40° SR (degrees Schopper-Riegler). The slurry is then exactly adjusted to a high density dry content of 2.5% by adding water. 5 parts of a 2.5% aqueous solution of the dyestuff obtained in step h) of Example 85 are added to 200 parts of the above resulting slurry. The mixture is stirred for about 5 minutes and, after addition of 2% (by weight) resin size and then 4% (by weight) alum (based on the dry weight), stirring is continued for a few minutes until the mixture is homogeneous. The resulting pulp is diluted with 500 parts of water to a volume of 700 parts and then used for the production of paper sheets by suction on a sheet former. The resulting paper sheets are dyed a brilliant blue. The waste water exhibits a substantially low residual dye concentration.

In a similar manner as described in Application Example F the dyestuffs according to Examples 1–84 and 86–134 may be used for dyeing paper.

APPLICATION EXAMPLE G 100 parts of cotton tricot, which have been dyed with the dyestuff of Example 1 analogously to the method of example F in ca. 1/1 standard depth, are mixed without intermediate drying in 1000 parts of tap water at 25° C. with 5 parts of sodium chloride and 4 parts of an after-treatment agent obtained from the reaction of diethylenetriamine with dicyanodiamide. The pH value of the dye bath is set at 6.5–7. The bath is heated to 60° C. over the course of 20 minutes, and this temperature is maintained for a further 20 minutes. Afterwards, the material is rinsed with cold tap water. The red cotton dyeing which has been after-treated in this way has perfect washing fastness and very good light fastness.

In a similar manner as described in Application Example G the dyestuffs according to Examples 2–134 may be used for dyeing cotton.

APPLICATION EXAMPLE H

A cotton dyeing produced with the dyestuff of Example 1 analogously to the method of example F in 1/1 standard depth, is impregnated on a padder with a solution, which contains 100 g/l of an after-treatment agent obtained by reacting the after-treatment agent of Application Example G with dimethyloldihydroxyethyleneurea and a hardening catalyst, and it is squeezed out to a pick-up of ca. 80%. It is subsequently shock-dried for 45 seconds on a stenter at a temperature of 175° C.–180° C. The yellow cotton dyeing thus obtained is notable for its perfect washing fastness. At the same time, there is a considerable improvement in the creasing fastness, and reduced swelling value of the cellulosic fibres.

In a similar manner as described in Application Example H the dyestuffs according to Examples 2–134 may be used for dyeing cotton.

APPLICATION EXAMPLE I

Water is added to a dry pulp in a Hollander consisting of 50% (by weight) of chemically bleached sulphite cellulose obtained from pinewood and 50% (by weight) of chemically bleached sulphite cellulose obtained from birchwood, and the slurry is ground until a degree of grinding of 35° SR is reached. The slurry is then adjusted to a high density dry content of 2.5% by adding water, and the pH of this suspension is adjusted to 7.

10 parts of a 0.5% aqueous solution of the dyestuff obtained in step (h) of Example 85 are added to 200 parts of the above resulting slurry, and the mixture is stirred for 5 minutes. The resulting pulp is diluted with 500 parts water and then used for the production of sheets by suction on a sheet former. The paper sheets thus obtained have a brilliant blue shade.

By a method analogous to that described in Application Example I further dyestuffs may be used consisting of any one of the dyestuffs of Examples 1–84 and 86–134. In all cases, paper sheets are formed having a brilliant blue shade.

APPLICATION EXAMPLE J 2.5 parts of the dyestuff obtained in Example 86 are dissolved with stirring at 25° C. in a mixture of 20 parts diethyleneglycol and 77.5 parts water to obtain a printing ink suitable for ink jet printing.

This application method is suitable for all Examples.

What is claimed is:

1. A compound of formula (I)

wherein $R_1$ is —$NH_2$ or wherein $R_5$ is hydrogen or $C_{1-4}$alkyl,

X and Y independently are halogen or hydroxy or $C_{1-3}$alkoxy or phenoxy or the radical of a cyclic, an aliphatic, an araliphatic or an aromatic amine linked over the amine-nitrogen and optionally substituted by hydroxy, carboxy, alkoxy, alkyl and/or sulphonic acid groups or the moiety of a heterocyclic amine linked over the amino-nitrogen, Z is halogen or the radical of a cyclic, an aliphatic, or an araliphatic amine linked over the amine-nitrogen and optionally substituted by hydroxy, carboxy, alkoxy and/or sulphonic acid groups or the moiety of a heterocyclic amine linked over the amine-nitrogen, $R_2$ is —$NH_2$ or with the same definitions for $R_5$, X and Y as above, or $R_2$ is the moiety (b)

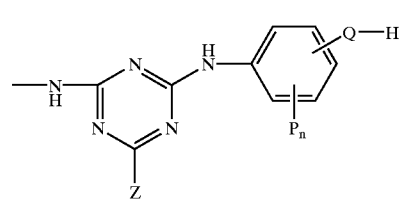

wherein P is —$SO_3H$, —COOH or —OH,
Q is a —NH— radical or is selected from the group consisting of:

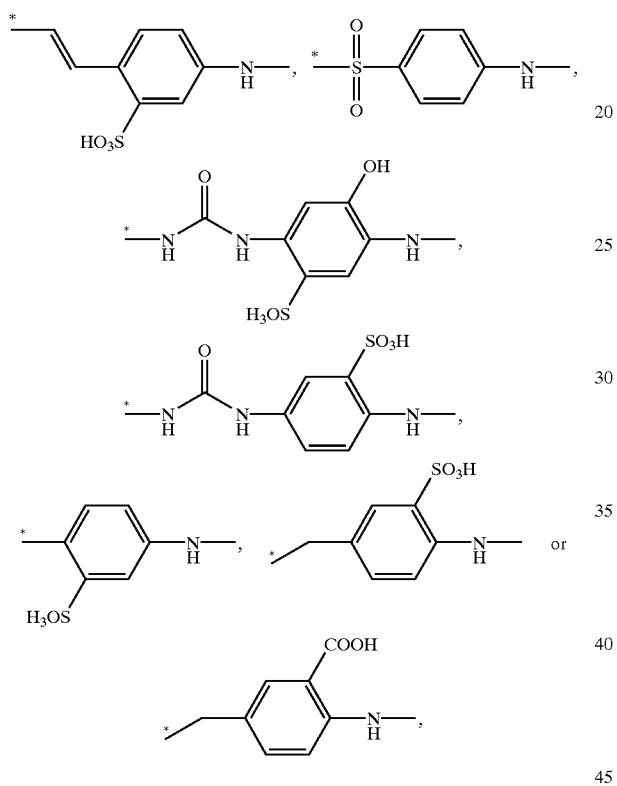

wherein the asterisk marks the bond attached to the phenyl ring,
Z is the same as above,
n has the value 1 or 2,
$R_3$ is —$NR_6$, in which $R_6$ is hydrogen or a $C_{1-4}$alkyl radical or $R_3$ is the moiety (a)

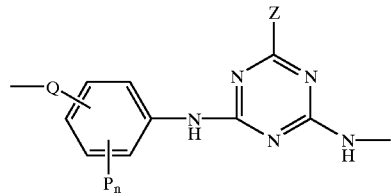

wherein all substituents have the same meaning as defined above,
$R_4$ is hydrogen or $C_{1-4}$alkyl,
$T_1$ and $T_2$ are independently hydrogen, halogen, $C_{1-6}$alkyl or $C_{1-4}$alkoxy,
M is hydrogen or a cation, with the proviso that
(i) when $R_1$ and $R_2$ are both —$NH_2$ then $R_3$ is

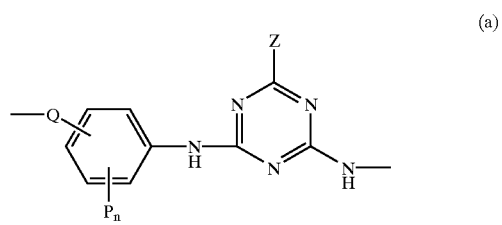

wherein all substituents have the same meaning as defined above,
(ii) when $R_1$ is —$NH_2$ and $R_2$ is

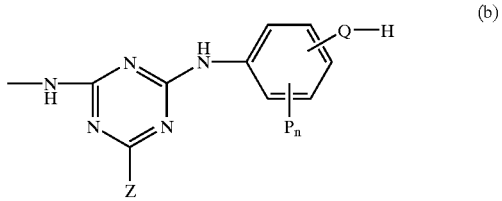

wherein all substituents have the same meaning as defined above then $R_3$ is —NH—; or a salt thereof, or a mixture of such compounds.

2. A compound of formula (I)

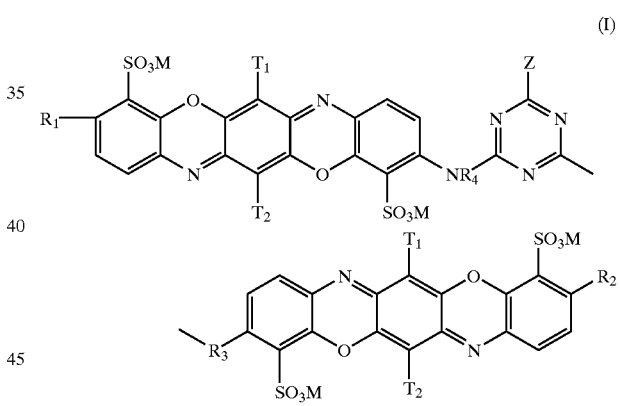

wherein both $R_1$ and $R_2$ are

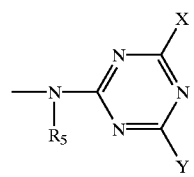

wherein $R_5$ is hydrogen or $C_{1-4}$alkyl and $R_3$ is —$NR_6$, wherein $R_6$ signifies hydrogen or a $C_{1-4}$alkyl radical,
X and Y independently are halogen or hydroxy or $C_{1-3}$alkoxy or phenoxy or the radical of a cyclic, an aliphatic, an araliphatic or an aromatic amine linked over the amine-nitrogen and optionally substituted by hydroxy, carboxy, alkoxy, alkyl and/or sulphonic acid groups or the rest of a heterocyclic amine linked over the amine-nitrogen, Z is halogen or the radical of a cyclic, an aliphatic, or an araliphatic amine linked over the amine-nitrogen and optionally substituted by hydroxy, carboxy, alkoxy and/or sulphonic acid groups or the rest of a heterocyclic amine linked over the amine-nitrogen, $R_4$ is hydrogen or $C_{1-4}$alkyl, $T_1$ and $T_2$ are independently hydrogen, halogen, $C_{1-6}$alkyl or $C_{1-4}$alkoxy, M is hydrogen or a cation.

3. A mixture containing

A) a compound of formula (Ia)

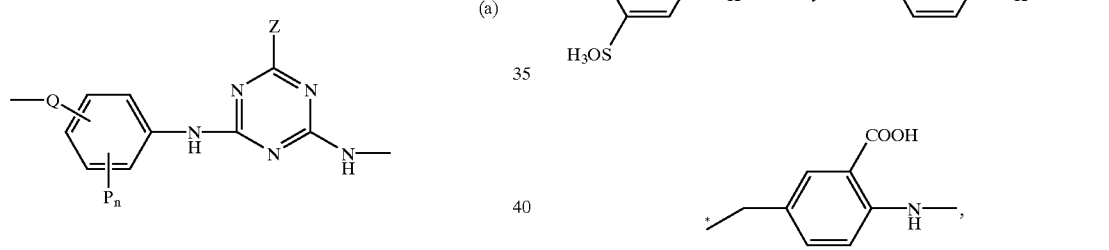

(Ia)

wherein $R_3'$ is a divalent radical of moiety (a)

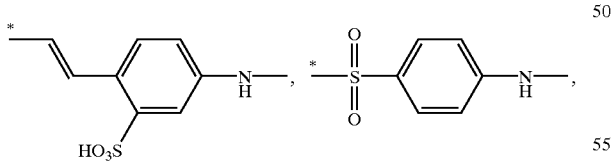

(a)

Q is a —NH— radical or is selected from the group consisting of:

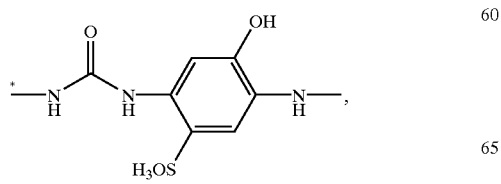

-continued

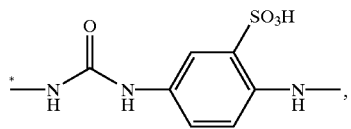

-continued

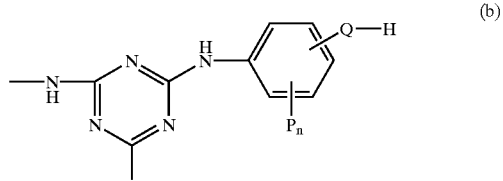

wherein the asterisk marks the bond attached to the phenyl ring;

Z is halogen or the radical of a cyclic, an aliphatic, or an araliphatic amine linked over the amine-nitrogen and optionally substituted by hydroxy, carboxy, alkoxy and/or sulphonic acid groups or the rest of a heterocyclic amine linked over the amine-nitrogen, P is —SO$_3$H, —COOH or —OH, n has the value 1 or 2, $R_2'$ is —NH$_2$, B) a compound of the above formula (Ia) wherein $R_3'$ is —NH—, $R_2'$ is a radical of moiety (b), (b)

wherein all substituents have the same meaning as defined above,

C) a compound of formula (II)

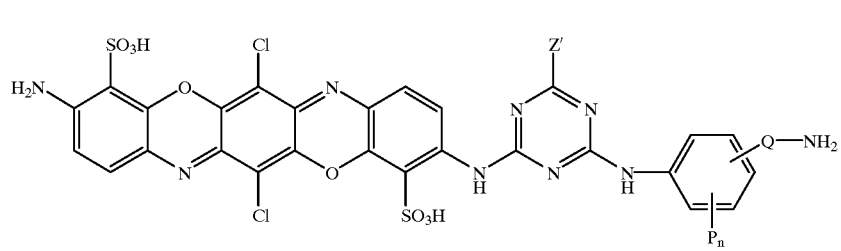

(II)

wherein Q, P and n have the same meaning as defined above and Z' has the same definition as Z, additionally Z' an be an aromatic amine, D) a compound of formula (II) wherein Z' has the meaning as defined above, except halogen, E) a compound of formula (III)

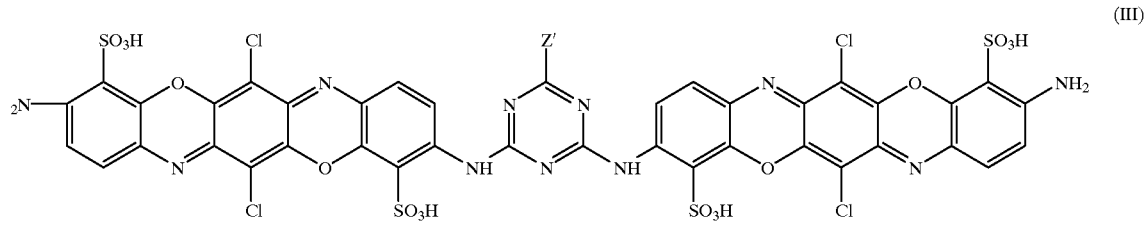

(III)

wherein Z' has the same definition as Z, additionally Z' can be an aromatic amine, or a salt of such compounds.

4. A mixture according to claim 2 containing about
30–40% by weight, of component A),
30–47% by weight, of component B),
1.5–8% by weight of component C),
2–11% by weight, of component D), and
12.5–23.5% by weight of component E); all as an alkali metal sat.

5. A composition for dyeing or printing a substrate or as a component of a printing ink comprising the compound or mixture of compounds of claims 1, in a carrier suitable for an ink-jet ink.

* * * * *